United States Patent

Bergmann et al.

Patent Number: 5,525,743
Date of Patent: Jun. 11, 1996

[54] PREPARATION OF ANTHRAQUINONE IMIDE COMPOUNDS

[75] Inventors: Udo Bergmann, Bensheim; Helmut Hoch, Weisenheim; Heike Kilburg, Speyer; Reinhold Kohlhaupt, Frankenthal; Matthias Niedenbrueck, Limburgerhof, all of Germany

[73] Assignee: BASF Aktiengesellschaft, Ludwigshafen, Germany

[21] Appl. No.: 328,948

[22] Filed: Oct. 21, 1994

[30] Foreign Application Priority Data

Oct. 21, 1993 [DE] Germany ............ 43 35 975.2

[51] Int. Cl.$^6$ ............ C09B 1/00; C07C 103/76
[52] U.S. Cl. ............ 552/214; 552/215; 552/216; 552/217
[58] Field of Search ............ 552/214, 215, 552/216, 217

[56] References Cited

U.S. PATENT DOCUMENTS

| | | |
|---|---|---|
| 3,040,063 | 6/1962 | Walker . |
| 4,382,034 | 5/1983 | Reubke et al. ............ 552/214 |
| 4,692,278 | 9/1987 | Blattner ............ 552/214 |

FOREIGN PATENT DOCUMENTS

| | | |
|---|---|---|
| 0047205 | 3/1982 | European Pat. Off. . |
| 0119956 | 9/1984 | European Pat. Off. . |
| 0136981 | 4/1985 | European Pat. Off. . |
| 0199670 | 10/1986 | European Pat. Off. . |
| 0326866 | 8/1989 | European Pat. Off. . |
| 0375990 | 7/1990 | European Pat. Off. . |
| 0382053 | 8/1990 | European Pat. Off. . |
| 654536 | 4/1929 | France . |
| 696425 | 9/1940 | Germany . |
| 208953 | 3/1940 | Switzerland . |

OTHER PUBLICATIONS

Fiat Final Report 1313II, Trianthrimid For Indanthrene Brown BR P. 102, 182, 1948.

BIOS Final Report 987 Indanthrene Direct Black RB (39) P. 63,71,76, 6–8–93, 1946.

*Primary Examiner*—Rebecca Cook
*Attorney, Agent, or Firm*—Oblon, Spivak, McClelland, Maier & Neustadt

[57] ABSTRACT

The preparation of anthraquinone imide compounds by condensation of anthraquinone compounds containing at least one primary amino group with halogenized aromatics or by condensation of halogenized anthraquinone compounds with primary aromatic amines, in the presence of a vat-dyeing catalyst and an acid-binding agent in an organic solvent, in which the organic solvent used is an alkyl benzoate.

4 Claims, No Drawings

PREPARATION OF ANTHRAQUINONE IMIDE COMPOUNDS

The present invention relates to a novel process for the preparation of anthraquinone imide compounds by condensation of anthraquinone compounds containing at least one primary amino group with halogenized aromatics or by condensation of halogenized anthraquinone compounds with primary aromatic amines, in the presence of a vat-dyeing catalyst and an acid-binding agent in an organic solvent.

Anthraquinone imides are important starting points for vat dyes or are themselves vat dyes known in the art, which are frequently used for dyeing or printing cotton or blended cotton fabrics.

The preparation of anthraquinone imides takes place, as is well known, by condensation of an anthraquinone substituted by at least one primary amino group with a corresponding halogenized aromatic reactant, a vat-dyeing catalyst and an acid-binding agent usually being added to the reaction mixture.

Well-known solvents for this reaction are naphthalene (BIOS Final Report 987, pp. 71 and 76, and 1493, p. 32, DR 696,425) and nitrobenzene (BIOS Final Report 987, p. 63, FIAT Final Report 1313 I, pp. 102 and 182, FR-A 654,536, CH-A 208,953, U.S. Pat. No. 3,040,063).

These prior solvents have a number of drawbacks, however: naphthalene sublimes at the high temperatures required for the condensation, for which reason the synthesis equipment must be subjected to elaborate purifying measures, in order to avoid technical disorders caused, e.g., by choking of conduits. Moreover, naphthalene adheres to the products of the reaction very stubbornly and must be removed by technically elaborate steam distillation.

Condensation reactions in nitrobenzene frequently demand long reaction times to achieve quantitative conversion, which is frequently not attainable, however, so that the end products are contaminated by unconverted educts and other by-products and, if at all possible, must be subjected to expensive purifying methods or produce end dyes having a lower coloristic index.

Thus different techniques have been proposed to overcome the aforementioned problems arising during synthesis in nitrobenzene. Thus E-A 119,956 describes portionwise metering of the catalyst during the reaction at from 195° to 205° C. and E-A 136,981 proposes subsequent thermal treatment of the reaction mixtures at from 215° to 250° C. unter pressure. Finally, E-A 199,670 states that it is advantageous to suspend the educts first of all in nitrobenzene at room temperature and then to add the suspension to a further quantity of nitrobenzene, heated to the temperature of reaction, such that the temperature can be maintained at approximately 210° C. These procedures are, however, also unsatisfactory, since they require elaborate chemical engineering (additionaly boilers, metering at boiling temperature, pressure equipment).

Of no less importance is the particularly important drawback incurred when using nitrobenzene, i.e. its danger to health, which makes it necessary to execute elaborate safety precautions with regard to the reaction equipment and to effect complete removal of the nitrobenzene from the products, which demands long treatment periods.

It was thus the object of the invention to overcome the aforementioned drawbacks.

Accordingly, there has been found a process for the preparation of anthraquinone imide compounds by condensation of anthraquinone compounds containing at least one primary amino group with halogenized aromatics or of halogenized anthraquinone compounds with primary aromatic amines in the presence of a vat-dyeing catalyst and an acid-binding agent in an organic solvent, wherein the organic solvent used is an alkyl benzoate.

The nature of the alkyl radical in the alkyl benzoates used as solvents according to the invention is not generally important provided the esters are liquid under the reaction conditions. Suitable alkyl benzoates are, in particular, $C_1$–$C_6$-alkyl benzoates such as hexyl, n-, iso- and sec-pentyl-, n-, iso- and sec-butyl and n- and iso-propyl benzoates, preferably ethyl benzoate and more preferably methyl benzoate. If desired, mixtures of said alkyl benzoates may be used.

The amount of solvent used is usually from 1 to 15 kg and preferably from 3 to 10 kg of condensation product.

The process of the invention is of particular significance for the preparation of anthraquinone imide compounds of the formula I

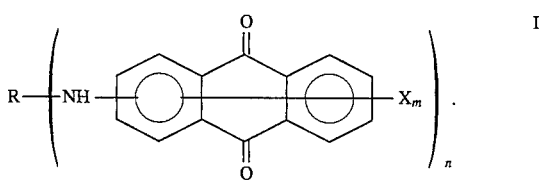

The radical R denotes, in particular, aromatic radicals such as are common in vat dyes. Specific examples thereof are anthraquinone, benzanthrone, anthanthrone, pyranthrone, dibenzanthrone (=violanthrone), isodibenzanthrone, anthraquinoneacridone (=phthaloylacridone), flavanthrone, fluoroanthene and dibenzpyrenequinone radicals. Also suitable are radicals of condensates of these aromatics, for example, halopyranthrone condensed with aminodibenzanthrone.

The radical n can carry substituents usual in vat dyes. These are substantially the same as the substituents X on the anthraquinone radicals.

Suitable radicals X are, e.g., halogen, primarily chlorine and bromine, hydroxy, amino, $C_1$–$C_4$ alkylamino, primarily methylamino and ethylamino, $C_1$–$C_4$ alkanoylamino, primarily acetylamino and propionylamino, benzoylamino, benzoylamino substituted by halogen or $C_1$–$C_4$ alkyl such as p-chlorobenzoylamino and p-methylbenzoylamino, and $C_1$–$C_4$ alkyl, primarily methyl and ethyl.

The anthraquinone radicals can carry up to four such substituents and preferably carry up to two substituents.

Finally, the variable n denotes integers from 1 to 4 depending on the nature of the aromatic radical R.

The preparation of the anthraquinone imides can be effected either by condensation of an anthraquinone substituted by at least one primary amino group with a halogenized aromatic compound or by condensation of a halogenized anthraquinone with a primary aromatic amine. The first variant is usually preferred.

As examples of preferred amine components mention may be made of 2-aminoanthraquinone, 2-amino-3-bromoanthraquinone, 2-amino-3-methylanthraquinone, and 2-amino-3-hydroxyanthraquinone and in particular of 1-aminoanthraquinone, 1,4- and 1,5-diaminoanthraquinones, 1-amino-4-benzoylaminoanthraquinone, and 1-amino-5-benzoylaminoanthraquinone as well as aminoviolanthrone.

Preferred halogen components, i.e. usually chlorinated and/or brominated compounds, are, for example, 1-chloroanthraquinone, 1,4- and 1,5-dichloroanthraquinones, 3-bromo- and 3-chloro-benzanthrones, 3,9-dibromo and 3,9-dichlorobenzanthrones, bromodichloroanthraquinone acridone, bromoanthraquinone acridone, dibromofluoroanthene, tetrabromopyranthrone, and dibromoviolanthrone.

The amine component, or if desired a mixture of different amine components, and the halogen component are preferably used in stoichiometric amounts, although an excess of up to approximately 20% of one of the components is possible, however.

The condensation reaction is advantageously carried out in the presence of a vat-dyeing catalyst and an acid-binding agent.

Suitable catalysts are copper compounds such as copper(I) acetate, copper(I) bromide, copper(I) chloride, preferably copper(I) oxide and more preferably copper powder. There are usually used, per kilogram of condensation product, from 5 to 150 g of catalyst.

Suitable acid-binding agents are, e.g., magnesium oxide, calcium oxide, calcium hydroxide, sodium acetate, sodium dihydrogen phosphate and disodium hydrogen phosphate, and potassium dihydrogen phosphate and dipotassium hydrogen phosphate, particularly potassium carbonate and potassium phosphate and very particularly sodium carbonate and sodium phosphate. There are usually used, per kilogram of condensation product, from 0.15 to 1 kg of acid-binding agent.

In some cases, e.g., during the reaction of tetrabromopyranthrone, the presence of an oxidizing agent is recommendable. Particular examples thereof are aromatic nitro compounds, e.g., o-, m- and p-nitrobenzoic acids, methyl and ethyl o-, m- and p-nitrobenzoates, o-, m- and p-nitrochlorobenzenes, o-, m- and p-nitrophenols as well as o-, m- and p-nitrobenzenesulfonic acids and sodium salts thereof. Suitable amounts of oxidizing agent are generally from 0.1 to 0.3 kg per kilogram of condensation product.

The condensation reaction of the invention is generally carried out at from 150° to 250° C. Temperatures above the boiling point of the reaction mixture are reached in closed apparatus. However, it is preferred to operate at from 190° to 210° C. under standard pressure with refluxing of the solvent.

The reaction times required to complete conversion are, in the process of the invention, usually from 1 to 40 h, in particular from 3 to 20 h.

The process is advantageously carried out by placing the alkyl benzoate in the reaction vessel and adding the educts, the catalyst and the acid-binding agent and, optionally, oxidizing agent thereto and then stirring the mixture while it is heated to the desired temperature and keeping it at this temperature until the reaction has proceeded to completion.

The purification of the reaction mixture to isolate the products after cooling can take place in various ways. One possibility comprises steam distillation of the total batch to remove and recover the solvent by phase separation, and filtration of the product from the aqueous suspension. A further possibility consists in distilling off the solvent, optionally in vacuo, making a slurry of the residues in water, removing and recovering the residual solvent by steam distillation, and refiltering to isolate the product from the aqueous suspension. A final possibility is to remove the product directly from the reaction mixture by filtration, to form a slurry thereof in water and subject the suspension to steam distillation for the removal and recovery of the adhering solvent, and finally to refilter the aqueous suspension to isolate the product.

The process of the invention for the preparation of anthraquinone imides is superior to prior processes in that the reaction proceeds smoothly and auxiliary measures such as subsequent thermal processing of the reaction mixture under pressure are not required. Quantitative conversions are achieved, for which reason the condensates obtained are of high purity and are not contaminated by educts and by-products and can be directly used for dyeing or for a further reaction to form a dye. Furthermore, the reaction takes place in many cases distinctly faster (up to a factor of 2) than when using nitrobenzene.

Thus the process of the invention provides an advantageous, economical, and industrially unproblematic and environmentally acceptable method of preparing anthraquinone imides.

EXAMPLES

Preparation of various anthraquinone imides

EXAMPLE 1

A mixture of 500 g of methyl benzoate, 62 g of 3-bromobenzanthrone, 49 g of 1-aminoanthraquinone, 32 g of anhydrous sodium carbonate and 0.9 g of copper powder was heated to 200° C. with stirring and kept at this temperature for 6 h.

After cooling to room temperature, the solvent was completely removed by distillation with steam. Filtration of the aqueous suspension of the product and drying yielded 107 g of the anthrimide of the formula 1

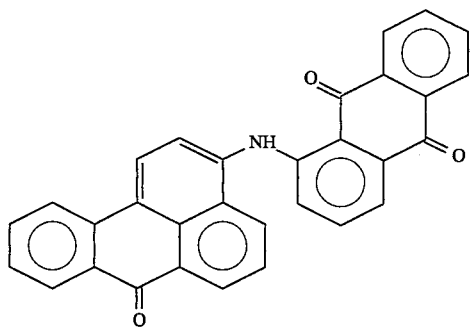

Acridine-cyclization in a fused alkali in the usual manner converted the anthrimide 1 to the dye C.I. Vat Green 3 having particularly high tinctorial strength, which dyed cotton with very good fastness properties.

EXAMPLE 2

A mixture of 530 g of methyl benzoate, 65 g of 3,9-dibromobenzanthrone, 77 g of 1-aminoanthraquinone, 27 g to anhydrous sodium carbonate and 1.0 g of copper powder was heated, with stirring, to from 200° to 205° C. and kept at this temperature for 22 h.

The reaction mixture was cooled to room temperature and then passed to a paddle dryer where the solvent was removed in vacuo by distillation. The residues were suspended in water, freed from residual solvent by steam distillation, isolated by filtration, and dried. There were obtained 139 g of the anthrimide of the formula 2

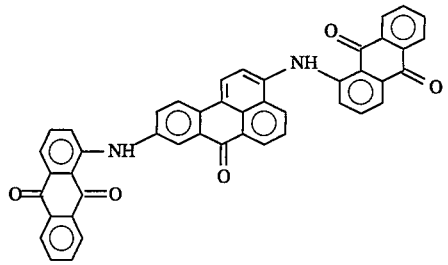

The anthrimide 2 yielded, following alkaline acridine-cyclization, the dye C.I. Vat Black 25 in good quality.

EXAMPLE 3

A mixture of 700 g of methyl benzoate, 100 g of 3-bromobenzanthrone, 80.6 g of 1,5-diaminoanthraquinone, 45 g of anhydrous sodium carbonate and 1.5 g of copper powder was heated with stirring to 200° C. over a period of 4 h.

Following cooling, the solvent was completely removed by steam distillation. Filtration and drying yielded 158 g of the anthrimide of the formula 3

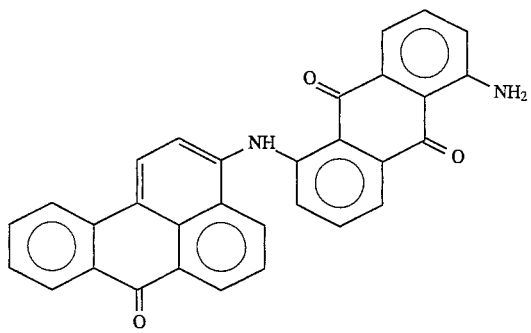

3

Following acridine-cyclization and subsequent benzoylation of the amino group there was obtained the corresponding olive vat dye having very high tinctorial strength.

Repetition of example 3 in nitrobenzene, however, yielded a dye having 40% lower tinctorial strength.

EXAMPLE 4

A mixture of 550 g of methyl benzoate, 66 g of 1-chloroanthraquinone, 61 g of 1-aminoanthraquinone, 26 g of anhydrous sodium carbonate and 1.5 g of copper(I) chloride was refluxed with stirring for 6 h.

Following cooling, removal of the solvent by steam distillation, filtering, and drying, there were obtained 116 g of the anthrimide of the formula 4

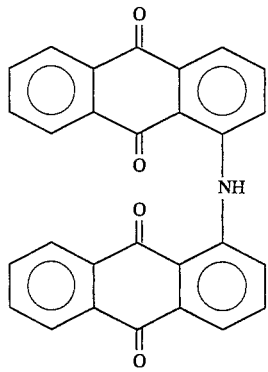

4

It was possible to process the anthrimide 4 to produce vat dye C.I. Vat Black 27 of good quality.

EXAMPLE 5

A mixture of 240 g of methyl benzoate, 33.7 g of 1-chloroanthraquinone, 15.7 g of 1,4-diaminoanthraquinone, 7.6 g of anhydrous sodium acetate, 7.3 g to anhydrous sodium carbonate and 0.5 g of copper powder was refluxed with stirring for 6 h.

After cooling to room temperature, the reaction mixture was filtered, the residues stirred into water and the adhering solvent removed with steam. Filtering and drying yielded 35 g of the trianthrimide of the formula 6

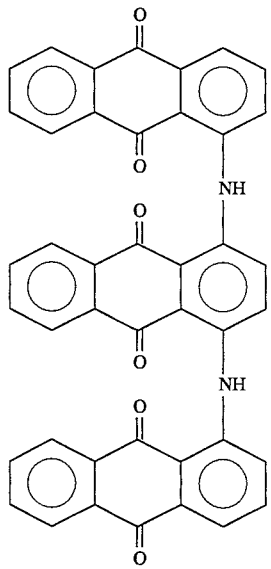

5

The trianthrimide 5 is a precursor of the vat dye C.I. Vat Brown 1.

EXAMPLE 6

A mixture of 1890 g of methyl benzoate, 132 g of 1,5-dichloroanthraquinone, 195 g of 1-aminoanthraquinone, 90 g of anhydrous sodium carbonate and 2.5 g of copper powder was heated with stirring to 200° C. over a period of 8 h.

Following steam distillation to remove the solvent, filtration, and drying there were obtained 325 g of the trianthrimide of the formula 6

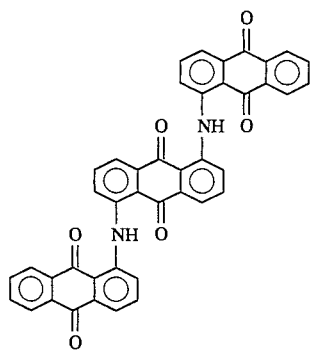

6

Carbozolation produced the vat dye V.I. Vat Orange 11 in good quality.

EXAMPLE 7

A mixture of 740 g of methyl benzoate, 80.0 g of bromodichloroanthraquinone acridone, 56.3 g of 1-amino-5-benzoylaminoanthraquinone, 37.5 g of anhydrous sodium carbonate and 1.7 g of copper powder was heated with stirring to 190° C. over a period of 4 h and subsequently passed to a paddle dryer.

Following the removal, by distillation, of the solvent in vacuo the residues were slurried in water, freed from solvent residues by steam distillation, isolated by filtration, and dried.

There were obtained 105 g of the anthrimide of the formula 7

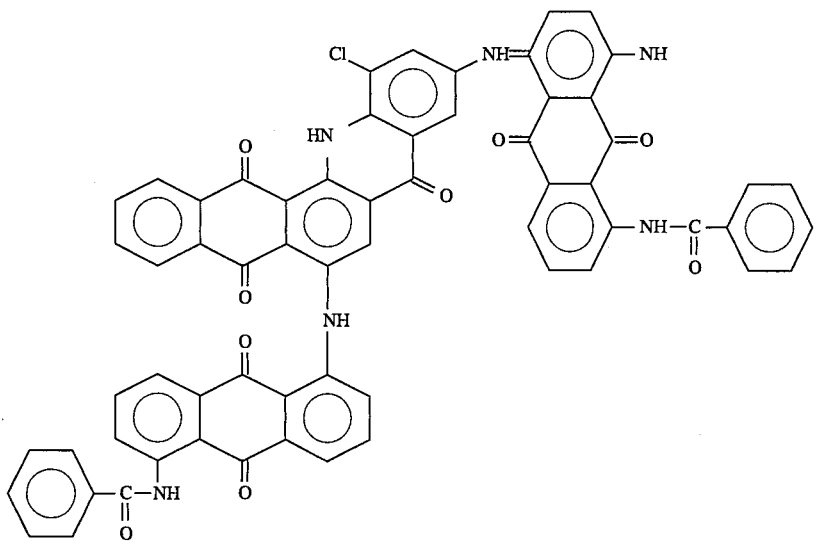

7

Subsequent carbozolation in sulfuric acid yielded the extremely light-fast vat dye C.I. Vat Brown 55 in very good coloristic quality.

When using nitrobenzene instead of methyl benzoate, the reaction time was up to 8 h and it was frequently not possible to achieve complete conversion.

EXAMPLE 8

A mixture of 807 g of methyl benzoate, 72.2 g of bromoanthraquinone acridone, 67.2 g of 1-amino-5-benzoylaminoanthraquinone, 46 g of anhydrous sodium carbonate and 1.7 g of copper powder was heated with stirring to 190° C. over a period of 12 h.

Purification in a manner similar to that described in Example 7 yielded 123 g of the anthrimide of the formula 8

EXAMPLE 9

A mixture of 890 g, of methyl benzoate, 106 g of dibromofluoroanthene, 152 g of 1-amino-4 -benzoylaminoanthraquinone, 223 g of anhydrous trisodium phosphate and 15.3 g of copper powder was heated with stirring to 175° C. over a period of 24 h.

Following steam distillation to remove the solvent, filtering, and drying there were obtained 245 g of the anthrimide of the formula 9

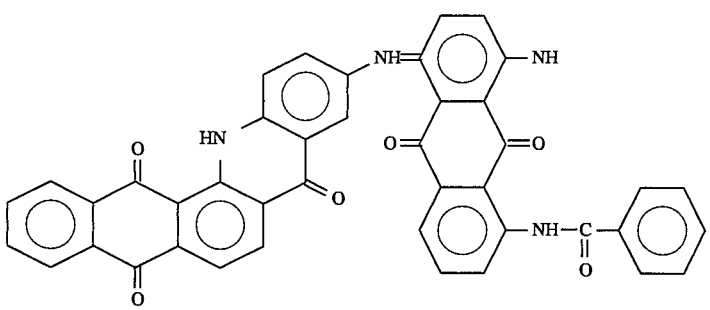

8

Subsequent carbozolation in sulfuric acid yielded the corresponding brown vat dye in good quality.

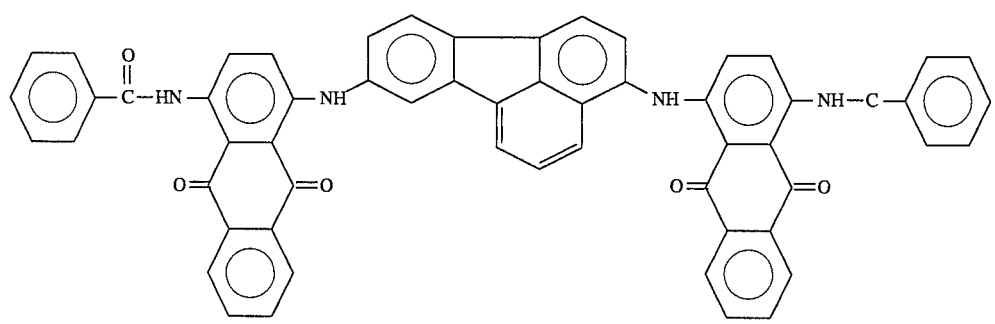

Carbozolation in sulfuric acid yielded the corresponding brown vat dye in good quality.

EXAMPLE 10

A mixture of 240 g of methyl benzoate, 10 g of tetrabromopyranthrone, 12.9 g of aminoviolanthrone, 6.7 g, of 1-aminoanthraquinone, 5.6 g of anhydrous sodium carbonate, 2.7 g of copper(I) oxide and 4 g, of sodium m-nitrobenzenesulfonate was heated with stirring to 200° C. over a period of 20 h.

Subsequent steam distillation, filtering, and drying yielded 27.6 g of the vat dye C.I. Vat Black 9 (formula 10)

Following the removal of the solvent by steam distillation the dye was isolated by filtration, decoppered by heating for three hours in 2500 mL of 10 wt % strength hydrochloric acid under reflux, again isolated by filtration and dried. There were obtained 151.3 g of the dye corresponding black vat dye of the formula 11

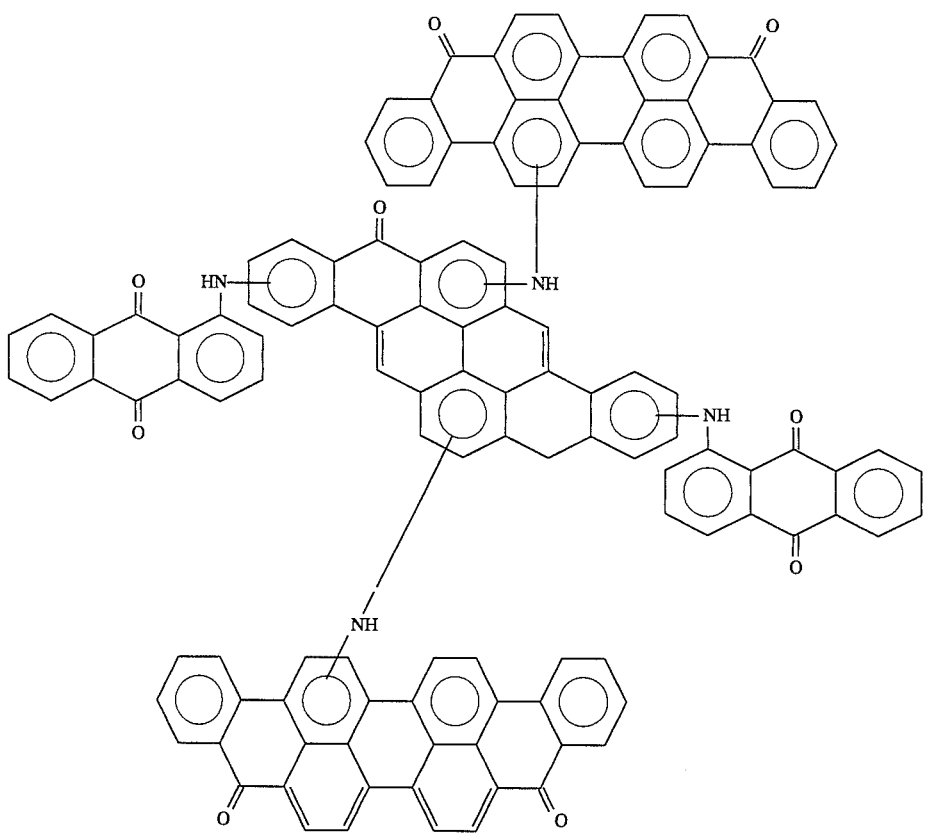

EXAMPLE 11

A mixture of 1300 g of methyl benzoate, 103.6 g dibenzanthrone brominated in sulfuric acid (bromine content 27.8 wt %), 80.3 g of 1-aminoanthraquinone, 57.3 g of anhydrous sodium carbonate and 25 g of copper(I) chloride was refluxed with stirring over a period of 20 h.

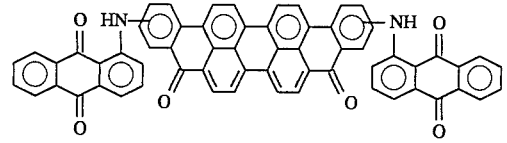

We claim:

1. A process for the preparation of an anthraquinone imide compound, comprising condensation of an anthraquinone compound containing at least one primary amino group with a halogenized aromatic compound or by condensation of a halogenized anthraquinone compound with a primary aromatic amine, in the presence of a vat-dyeing catalyst and an acid-binding agent in an organic solvent, wherein the organic solvent used is an alkyl benzoate.

2. A process as defined in claim 1, wherein the organic solvent used is methyl benzoate.

3. A process as defined in claim 1 further comprising conducting said condensation in the presence of an oxidizing agent.

4. The process of claim 1, wherein said anthraquinone imide compound is of the formula I

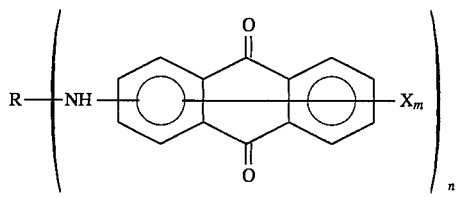

wherein R is phenyl, anthraquinone, benzanthrone, anthanthrone, pyranthrone, dibenzanthrone, isodibenzanthrone, anthraquinone acridone, flavanthrone, fluoroanthene, dibenzpyrenequinone or a condensation product thereof, each of which may be optionally substituted with a halogen, hydroxy, $C_1$–$C_4$ alkyl, amino, $C_1$–$C_4$ alkylamino, $C_1$–$C_4$ alkynoylamino, benzoylamino, or benzoylamino substituted with halogen or $C_1$–$C_4$ alkyl, X is halogen, hydroxy, $C_1$–$C_4$ alkyl, amino, $C_1$–$C_4$ alkylamino, $C_1$–$C_4$ alkanoylamino, benzoylamino, or benzoylamino substituted with halogen or $C_1$–$C_4$ alkyl, m is an integer from 1 to 4, and n is an integer from 1 to 4.

* * * * *